United States Patent [19]

Kallies

[11] 4,298,688
[45] Nov. 3, 1981

[54] TEST DEVICE FOR THE DETECTION AND DETERMINATION OF GLUCOSE

[75] Inventor: Karl-Heinz Kallies, Sebnitz, German Democratic Rep.

[73] Assignee: Veb Arzneimittelwerk Dresden, Radebeul, German Democratic Rep.

[21] Appl. No.: 68,323

[22] Filed: Aug. 20, 1979

[30] Foreign Application Priority Data

Jul. 25, 1978 [DD] German Democratic Rep. ... 206900

[51] Int. Cl.³ .............................................. C12Q 1/54
[52] U.S. Cl. ........................................ 435/14; 422/56; 422/57; 422/58; 435/25; 435/28; 435/805; 435/4
[58] Field of Search .................... 435/14, 28, 805, 25; 422/56, 57, 58, 59, 60

[56] References Cited

U.S. PATENT DOCUMENTS

| | | | |
|---|---|---|---|
| 3,050,373 | 8/1962 | Collins | 435/805 X |
| 3,066,081 | 11/1962 | Rorem et al. | 435/14 |
| 3,235,337 | 2/1966 | Artis | 435/25 X |
| 3,298,789 | 1/1967 | Mast | 435/805 X |
| 3,721,607 | 3/1973 | Gruber et al. | 435/14 |
| 3,785,929 | 1/1974 | Kronish et al. | 435/805 X |
| 4,094,647 | 6/1978 | Deutsch et al. | 422/56 |
| 4,137,049 | 1/1979 | Couch et al. | 422/56 |

*Primary Examiner*—Robert J. Warden
*Attorney, Agent, or Firm*—Michael J. Striker

[57] ABSTRACT

A test strip for the detection and determination of glucose in body fluids comprising a carrier demarcated into three zones (a) a measuring zone which is untreated, but may be impregnated with a coloring agent, oxidizing agent, buffer or precipitating agent, (b) a reaction zone containing glucose oxidase and (c) a detection zone composed of at least one strip containing peroxidase and an indicator. The paper test strip is preferably enclosed within a suitably dimensioned capillary tube which contains markings at the end thereof enclosing the measuring zone for limiting the amount of flow liquid to be admitted and additional markings at the end thereof enclosing the detection zone for quantitatively reporting the glucose content.

11 Claims, 4 Drawing Figures

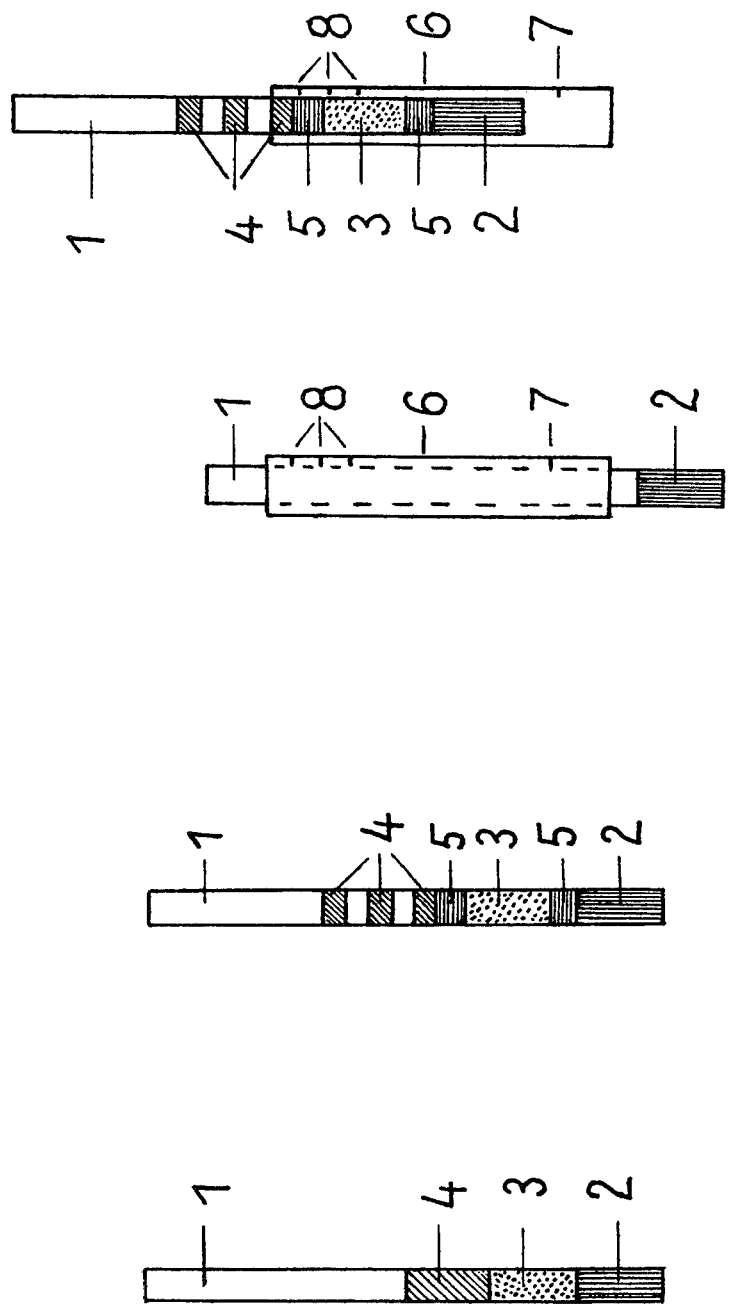

TEST DEVICE FOR THE DETECTION AND DETERMINATION OF GLUCOSE

This invention relates to a test device for use in the detection and determination of glucose in body fluids.

The invention more particularly relates to a test strip for use in the detection and determination of glucose in body fluids which advantageously is provided enclosed in a capillary tube.

The enzymatic decomposition of glucose using the enzyme glucose oxidase and its detection by means of specific indicators in the presence of the auxiliary enzyme peroxidase or other similarly acting substance is known, as is the use of test strips applying these same principals.

These known analytical procedures are always based on color reactions which can be visually or photometrically evaluated. When lower glucose concentrations are involved, the color reactions are readily differentiable, however with increasing glucose amounts as occurs in certain pathological conditions, the color gradations are difficult to appreciate. As a result the heretofore described test strips in these pathologically important ranges provide no clear indication of the actual glucose concentration. It has been proposed that the test strips as available be modified so that the necessary components for the reactions involved be applied in a zone and the two reactions (glucose oxidase and peroxidase) be carried out parallel to one another. However with the resultant increased amount of substrate the micromilliens and the resultant diffusion take on considerable significance.

The procedures which have already been described for the detection of glucose involving the use of separate glucose oxidase and peroxidase indication zones are only suitable for making qualitative analyses and further possess the same disadvantage that the enzyme glucose oxidase and also the decomposition products of the reaction are diffused together with analysis liquid into the peroxidase zone. Further the optimum pH for both enzymes is different so that for the commonly carried components, no optimal conditions exist.

A further disadvantage of the known procedures lies in that, the thereby formed colored substances are with increasing reaction times further oxidized giving rise to mixed colors. Thus a lengthening of the reaction time not only does not serve to improve the results but in fact serves to worsen them. It has been suggested to ameliorate the disadvantages associated with the already described processes through the addition of gelatin, and of certain polymers, as well as through the selection of suitable buffers. To some extent, these provisions have worked an improvement, as has the visual evaluation been facilitated by the suggestion to employ certain yellow or red dyestuffs.

The evaluation or final determination of the presence and the amount of glucose in all of the heretofore described test procedures takes place by resort to a color chart or index or with the help of a special measuring apparatus in which case a standard measurement or determination must also be carried out. Further, in the instances of using the color charts or the measuring apparatus, the evaluations are dependent on the use of specific reaction times and reading times.

These disadvantages of poor differentiability, of the difficulties in correlating the color reactions to the color charts, the need to run standard or control reactions, the requirement for observing carefully regulated reaction and reading times are further added to and influenced by the decrease in the enzymatic activity and through the presence of disturbing substances in the material being analyzed. Further it has not been possible heretofore to use the same test strips or foils for carrying out the glucose determinations in urine, serum and blood. Using the known strips, the presence of albumin and of pigments require entirely different considerations in preparing the test strips. For this reason it has been necessary that the reaction zones be made hydrophobic or be covered with a semipermeable layer.

A special form of test strip for use in the detection of residual glucose in urine has already been evolved which is capable of distinguishing an absolutely glucose free urine from urine samples having physiological glucose amounts of up to 30 mg/100 ml (Journal of the American Medical Association, Apr. 15, 1968, Vol. 204, pp 205–208). In this procedure the carrier material, i.e. paper is pretreated with 2-diethylaminoethanol. The problem, however, still exists to determine in serum or blood, glucose amounts under 40 mg/100 ml, the same being an important diagnostic problem especially in pediatric therapeutics. This type of detection is not possible with the heretofore described test strips as in this low range, no visually (uninterfered with) readings result.

Series determinations are by the cojoint limitations of the reaction and reading times not possible by a single laboratory employee, thus seriously limiting the use of these test procedures. Inexperienced persons, such as for example old diabetics attempting to make the visual evaluations under the aforedescribed conditions to which can be added the inconvenience of the color chart, are seriously disadvantaged. This further markedly limits the broad application of these test strips in self-control programs.

It is an object of the invention to provide a test device with which a quantified uptake of the investigation liquid is made possible.

Another object of the invention is to provide a test device for the determination of glucose in which the final evaluation, i.e. reading, can be carried out directly at the time of the sampling or at some subsequent time.

Still another object of the invention is to provide a test device for the determination of glucose in which the final evaluation can be carried out directly at the time of the sampling or at some subsequent time thereby permitting single as well as series determinations to be made.

A further object of the invention is to provide a test device equally suitable for carrying out glucose determinations in urine, serum and blood.

Yet a further object of the invention is to provide a test device for the determination of glucose which provides a required and regulated amount of liquid to be analyzed, is not dependent for the final evaluation on the reaction time, includes the glucose oxidase in an economically suitable manner, requires no color charts or special instrumentation, is quantitatively accurate in the high glucose ranges as well as in the detection of low concentrations, i.e. under 40 mg/100 ml, in any of urine, serum or blood.

Additional objects of the invention, its scope, advantages, and the manner in which it may be practiced will be readily apparent to persons conversant with the art from the following description of exemplary embodiments thereof taken in conjunction with the subjoined claims and annexed drawings, in which:

FIG. 1 is a plan view of a test strip in accordance with the invention usable without a capillary tube;

FIG. 2 is a plan view of a test strip provided with indicator-signal zones usable with a capillary tube;

FIG. 3 is a plan view of a capillary tube with the test strip in place for taking up the liquid to be analyzed; and FIG. 4 is a plan view of a capillary tube with the test strip in place for taking up the circulating agent.

According to the invention there is now provided a test strip composed of at least three zones
 (a) a measuring zone,
 (b) a reaction zone, and
 (c) a detection zone.

The measuring zone serves for the taking up or absorption of a definite amount of the liquid to be evaluated. No reaction takes place in this zone.

This zone can additionally contain marking or coloring agents, oxidation agents, buffers, precipitation agents so that for instance albumin, blood pigments and Vitamin C can be bound thereby and eliminated as interferants.

Above the measuring zone and connected thereto is the reaction zone which has the glucose oxidase applied thereon. Surprisingly, it has been found that the glucose oxidase can be immobilized in this zone without any essential diminution of its activity if it is applied to the carrier in conjunction with an acid solution below its isoelectric point. The absorptive capacity of the test strip required as a prerequisite for the reaction principal is in no way diminished by this expedient. This fixing of the glucose oxidase is to be considered an important economic advantage as in this was no loss of enzyme takes place. It is also possible to immobilize the glucose oxidase on the carrier by applying the same as a suspension or by any other previously known method as long as it is maintained in this state in the subsequent procedure.

Following the reaction zone and annexed thereto is a detection zone. The detection zone contains the auxiliary enzyme peroxidase and the indicator applied thereon as a single stripe or in the form of several separate signal zones separated one from the other by intermediate spaces or stripes. If a number of peroxidase and indicator zones are applied to form the separate signal zones, then the intermediate spaces can be free of any substance or preferably can contain a pigment binding or fixing substance.

Between the measuring zone and the reaction zone, there can be provided a safety clearance zone which can contain a color or marking substance and can also be provided with reagents for buffering or masking.

Between the reaction zone and the detection zone, there can be inserted a neutral, not sensitized zone or a zone which contains a buffer substance.

The distances between the measuring zone and the reaction zone on the one side and the reaction zone and the detection zone on the other side can be varied or different.

For supporting or taking up the test strip, there is provided a capillary tube made of glass or a suitable synthetic material, i.e. plastic. At one of its ends (lower end), the capillary tube is provided with a colored marking which serves to indicate the level to which a determined amount of flow or circulating liquid is to be taken up. The capillary tube has a length of 40-120 mm, preferably 60 mm. It is provided with a constant inner diameter of 1-3 mm, preferably 2.5 mm. At its opposite or upper end, the capillary tube contains color markings or graduations. These markings serve for indicating the amount of glucose in the fluid being analyzed. The glucose concentration is equivalent to the length of the colored detection zone and it follows that a reading off of the graduated markings provides a quantitative glucose report.

If the test strip in accordance with the invention is used together with the capillary tube, then the observation of a definite reaction time is not necessary. For undertaking a glucose determination, the measuring zone portion of the test strip which projects out of the capillary tube is immersed in the fluid to be analyzed. The test strip can immediately or sometime after the absorption of the fluid to be analyzed into the measuring zone has taken place, be pulled back into the capillary tube. Thereafter the test strip through the taking up of a flow or circulating liquid up to the marking at the bottom of the capillary tube can be brought to the desired reaction.

The sampling and reaction courses are not dependent on each other. When the test strip is used together with the capillary tube, the test device can be held for a period of time before the uptake of the flow or circulating agent. This allows for the carrying out of a single or series of samplings as desired. By means of the capillary tube, it can be appreciated that a new and far reaching quantified sampling of the circulating liquid even by fairly unskilled, i.e. laypeople is made possible.

If the test strip is not intended for use with the capillary tube, it is most advantageous for the measuring reaction and detection zones to be arranged one after the other without any intermediate zone. The glucose detection in this case takes place by dipping the test strip in the liquid to be analyzed for the full length of the measuring zone and then evaluating the length of the colored indicators in the detection zone. This procedure permits at least the semiquantitative detection of glucose.

The test strips of the invention avoid the need for a color chart. The test strip is further so arranged that on the one hand the determination of very low glucose concentrations is made possible and on the other hand, the diffusion of the fluid being analyzed through the glucose oxidase zone by a substrate barrier is prevented, thus making possible the accurate determination of high glucose concentrations.

The following examples are given in order to illustrate the invention but are in no wise to be construed as limited thereby.

EXAMPLE 1

This example illustrates the semiquantitative detection of glucose in urine without resort to a color plate or guide and without any limits with respect to reaction time and reading time, adapted for use in carrying out single or serial determinations and utilizes the test strip embodiment as shown in FIG. 1.

As carrier material, there is employed a filter paper having a weight of 100 g/m$^2$. A 1% solution of Sudan red in ethanol is prepared and one end of the test strip 1 having a width amounting to 5-15 mm is marked therewith in the area constituting the measuring zone 2. The width of this zone 2 is accurately determined to correspond to the width selected for the following zone 3. In the example the width of zone 2 amounts to 10 mm.

Reaction zone 3 is prepared by depositing a solution manufactured by separately preparing (a) a solution of 0.1 g benzoic acid in 10 ml ethanol and (b) 3000 E glucose oxidase in 10 ml distilled water, mixing the two together and depositing the resultant solution above the 10 ml wide Sudan red zone to form a zone having a width of 3–10 mm and in this specific instance a width 5 mm.

The detection zone 4 is prepared by mixing together the following: (a) 300 E peroxidase and 10 ml buffer, 0.2 mol, pH 7.0, (b) 100 mg o-tolidine and 10 mg Auramine yellow dissolved in 10 ml ethanol and depositing the resultant solution on the paper strip above reaction zone 3. The solution as thus described can be deposited in stripes having widths of 1–2 mm, for example in four stripes arranged one above the other with intermediate spaces or as shown in the drawing in one zone having a width of 10 mm.

The deposition of the three solutions for forming the different zones suitably takes place using the known linear machines, the three zones being deposited simultaneously. The sheet of paper is thereafter dried in the known manner and cut up to form the strips. For using the test strip for carrying out a determination, the test strip 1 is dipped for a short period of time into the liquid to be analyzed for example, urine so that only the measuring zone 2 is inserted into the liquid. The amount of liquid taken up in this manner moves by capillary action up into and through the glucose oxidase zone into the peroxidase indicator zone, i.e. the liquid diffuses upwardly through the three zones. In this manner a definite amount of the glucose undergoes reaction and this amount is indicated in the peroxidase indicator zone. The length or the number of the colored peroxidase indicator zones, indicates the amount of glucose present in the test liquid. The reaction is terminated when the diffusion is completed and is dependent on the glucose content; the coloration resulting remaining constant even after the liquid has been evaporated.

The test strips can accordingly be optionally evaluated either at the time of making the test or at any time thereafter.

EXAMPLE 2

This example illustrates the manufacture of a test strip provided with indicator-signal zones and with a capillary tube and which is particularly adapted for determining glucose in urine, for individual regulation and also for serial determination without any requirement for a color index and without there being any fixed or defined reading time and is illustrated in FIG. 2.

A suitable carrier material having a good absorption capacity, for instance filter paper having a surface weight of 135 g/m² is simultaneously treated with the following solutions so that they are deposited one above the other on the paper.

Measuring zone 2, 10 mm width:

A solution, prepared by dissolving 0.1 g potassium permanganate and 100 mg Congo red in 100 ml distilled water is deposited at the lower edge of the sheet of filter paper to form a zone having a width of 10 mm. In this zone, the readily reduceable substances, for instance ascorbic acid which are present in the urine and which can disturb the glucose determination reaction are decomposed.

Intermediate zone 5, 5 mm width adjacent to and connected to measuring zone 2:

A solution of 1 g nitrolotriacetic acid in 100 ml of distilled water is prepared and is deposited on the strip as indicated to form a stripe 5 mm in width. The zone 5 thus formed serves as a masking zone.

Reaction zone 3, 10 mm in width:

A solution of 0.5 g succinic acid in 50 ml distilled water and a solution of 0.5 g glucose oxidase in 50 ml distilled water (corresponding to 1500 E) are prepared. The two solutions are then mixed together and deposited above the intermediate zone 5 to form a stripe 10 mm in width.

Intermediate zone 5, 5 mm in width adjoining and connected to reaction zone 3:

A solution of 1 g sodium acetate in 100 ml of water was prepared and this solution deposited so as to form a zone having a width of 5 mm. This zone 5 serves as a buffer zone.

Detection zone 4:

Connected to the intermediate zone 5, there are provided a plurality of peroxidase indicator zones having a width of 2–3 mm separated by intermediate zones having a width of 2–3 mm. The peroxidase indicator zones are prepared by separately forming two solutions having the following compositions:

(a) 100 mg peroxidase (corresponding to 600 E) dissolved in 50 ml of a 0.2 mol buffer solution having a pH of 7.2;

(b) 400 mg o-tolidine and 75 mg Orasol yellow in 50 ml ethanol.

These two solutions are mixed together and are thereafter in the same manner as described above deposited in separated stripes above the intermediate zone 5.

The deposition of the different solutions can take place in the known manner simultaneously or one after the other. The paper sheet thus prepared is dried and is then cut up into strips or bands having a width of 2 mm. The bands are then individually inserted into a capillary tube 6 made of glass or a suitable plastic. The capillary tube 6 is provided with markings 7 for measuring the flowing or circulating liquid. The capillary tube 6 has a length of 60 mm and an inner diameter of 2.5 to 3 mm.

Carrying out the determination, the measuring zone 2 which is colored red by the Congo red dye is manipulated so that it extends out of the capillary tube as shown in FIG. 3 and is then dipped for a very short period of time into the liquid to be analyzed.

There takes place a quantified liquid uptake. Eventually the available readily reduceable substances present in the liquid as for instance ascorbic acid, will be oxidized in this zone, however, the reaction of glucose will not and does not take place.

The strip is then drawn back into the capillary tube 6 so that the bottom edge lies above the marking 7 in the capillary tube 6 as for instance shown in FIG. 4.

According to whether a single determination or a serial determination is being carried out, the glucose determination is completed immediately or at a later time, as desired. For this purpose the capillary tube 6 is loaded with distilled water up to the marking 7 by dipping the arrangement into the water. Thereafter the test strip 1 is submerged in the water and is then placed in an upright position. Through capillary action, the fluid to be analyzed is diffused with the water through the different zones and the glucose present in the test liquid thus brought to reaction. According to the glucose content one or more of the indicator zones is colored and this can be read off by reference to the graduations 8 provided on the capillary tube. The diffusion process is terminated and it is possible to read off the resulting valve either at this point in time or at some later time as the coloration is fixed and remains constant.

The measuring zone 2 can be prepared with other suitable oxidation or precipitating agents in place of the potassium permanganate and even the marking agents can be varied in the known manner.

For detection zone 4, there can similarly be used any of the substances described in the literature having peroxidase activity.

The use of other known indicator systems for the detection of hydrogen peroxidase instead of the o-tolidine is also possible.

EXAMPLE 3

The manufacture of a test strip provided with indicator-signal zones for use in the detection and determination of trace amounts of glucose in urine in serum or in blood of children, without the requirement for a color chart or plate and without a fixed reading time is illustrated in FIGS. 2-4.

As the carrier, there is used a filter paper having a surface weight of 220 g/m$^2$.

Measuring zone 2:

1. Zone, 10 mm wide without any preparation,
2. Zone, 10 mm wide inpregnated with a solution of 0.05 g potassium permanganate in 100 ml of water.

Reaction zone 3, 10 mm wide:

Impregnated with a solution mixture of (a) 1 g benzoic acid in 50 ml ethanol, (b) 1 g glucose oxidase in 50 ml water (corresponding to 30,000 E).

Detection zone 4, 10 mm wide, annexed to the reaction zone 3:

This zone is impregnated with a mixture of the following solutions: (a) 200 mg peroxidase (corresponding to 600 E), dissolved in 50 ml 0.2 mol buffer solution having a pH of 7.2, (b) 1 g o-tolidine, 50 ml Orasol yellow dissolved in 50 ml ethanol.

These solutions for the different zones can be deposited either simultaneously or one after the other. After the carrier paper has been dried it is cut up into bands having a width of 2 mm and a length of about 70 mm and these bands or strips inserted into capillary tubes 6.

The capillary tube 6 has an inner diameter of 2.5-3 mm. They are so marked that when in use, 40 μl of the liquid to be analyzed is taken up therewith. The test strip 1 is drawn up so that it is positioned above the marking 7 in the capillary tube, the liquid to be analyzed taken up and the test strip inserted in this manner utilized for differentiating amounts of glucose. Amounts of glucose decreased below the physiologically normal levels can be determined in the liquid to be analyzed.

The quantitative evaluation is carried out by resort to the graduations 8 on the capillary tube 6.

I claim:

1. A test strip for the detection and determination of the concentration of glucose in samples of body fluids containing in addition Albumin, blood pigments or Vitamin C as interferants comprising, a carrier strip capable of transporting fluid therealong and which is separated into three zones arranged one above the other in the order indicated: (a) a measuring zone for receiving a predetermined amount of the test sample impregnated with at least one member of the group consisting of marking agents, coloring agents, oxidation agents, buffers and precipitating agents for binding and elimination of interferants, (b) a reaction zone containing glucose oxidase that will catalyze the oxidation of a glucose substiate, and (c) a detection zone containing peroxidase and an indicator for providing a visible response for accurately determining the level of glucose in the test sample.

2. A test strip according to claim 1, wherein said glucose oxidase is applied to said carrier in an acid solution below its isoelectric point.

3. A test strip according to claim 1, wherein said detection zone is composed of a plurality of indicator stripes containing peroxidase and indicator separated one from the other by untreated stripes.

4. A test device for the detection and determination of glucose in samples of body fluids comprising a test strip according to claim 1, enclosed within a capillary tube open at both ends thereof, bearing markings at the end thereof adjacent the measuring zone for measuring a predetermined amount of flow liquid to be admitted and additional markings at the other end thereof adjacent the detection zone for use in quantitatively reporting the glucose content in the sample of fluid analyzed.

5. A test device according to claim 4, wherein said glucose oxidase is applied to said carrier in an acid solution below its isoelectric point.

6. A test device according to claim 4, wherein in said test strip the detection zone is composed of a plurality of indicator stripes containing peroxidase and indicator separated one from the other by untreated stripes.

7. A test device according to claim 4, wherein in said test strip the detection zone is composed of indicator stripes containing peroxidase and indicator separated one from the other by intermediate stripes which contain a pigment binding agent.

8. A test device according to claim 4, wherein in said test strip the measuring zone and reaction zone are separated by a safety clearance zone containing at least one member of the group consisting of coloring agents, buffers and masking agents.

9. A test device according to claim 4, wherein in said test strip the reaction zone and detection zone are separated by at least one buffer impregnated safety clearance zone.

10. A test device according to claim 4, wherein said capillary tube has an inner diameter of 1-3 mm, a length of 40-120 mm and is made of glass or a glass clear plastic.

11. A test device according to claim 10, wherein said capillary tube has an inner diameter of 2.5 mm and a length of 60 mm.

* * * * *